United States Patent [19]

Boggs

[11] 4,049,730
[45] Sept. 20, 1977

[54] AMINE PROMOTERS FOR HYDROHALOGENATION

[75] Inventor: Jesse K. Boggs, Seabrook, Tex.

[73] Assignee: Exxon Research & Engineering Co., Linden, N.J.

[21] Appl. No.: 406,128

[22] Filed: Oct. 12, 1973

Related U.S. Application Data

[62] Division of Ser. No. 171,607, Aug. 13, 1971, Pat. No. 3,852,368.

[51] Int. Cl.² ............................................. C07C 17/08
[52] U.S. Cl. ................................... 260/663; 260/657
[58] Field of Search ........................................ 260/663

[56] References Cited

U.S. PATENT DOCUMENTS 1,202,282  10/1916  Graul .................................. 260/663
2,058,465  10/1936  Kharasch ............................. 260/663
2,628,934   2/1953  Raley et al. ......................... 260/663
3,065,242  11/1962  Alderson et al. .................... 260/663

Primary Examiner—Delbert E. Gantz
Assistant Examiner—Joseph A. Boska
Attorney, Agent, or Firm—S. W. Brock, Jr.; Y. S. Finkle

[57] ABSTRACT

Tertiary alcohols and Type III olefins are hydrohalogenated in the presence of an amine which acts as a reaction promoter. The amine speeds up the reaction between the hydrogen chloride and tertiary alcohol or olefin without unduly increasing the amount of polymer (sludge) formation.

Triethylamine and tributylamine have been found to be effective, particularly in promoting the hydrochlorination of tertiary alcohols.

12 Claims, 2 Drawing Figures

AMINE PROMOTERS FOR HYDROHALOGENATION

CROSS-REFERENCE TO RELATED APPLICATIONS

This is a division, of application Ser. No. 171,607, filed Aug. 13, 1971, Pat. No. 3,582,368.

The subject matter of this application is related to that described in my copending application Ser. No. 101,921 filed Dec. 28, 1970 and entitled "Selective Tertiary Alkylation of Aromatic Hydrocarbons" now U.S. Pat. No. 3,739,039.

THE DRAWINGS

Figure 1:
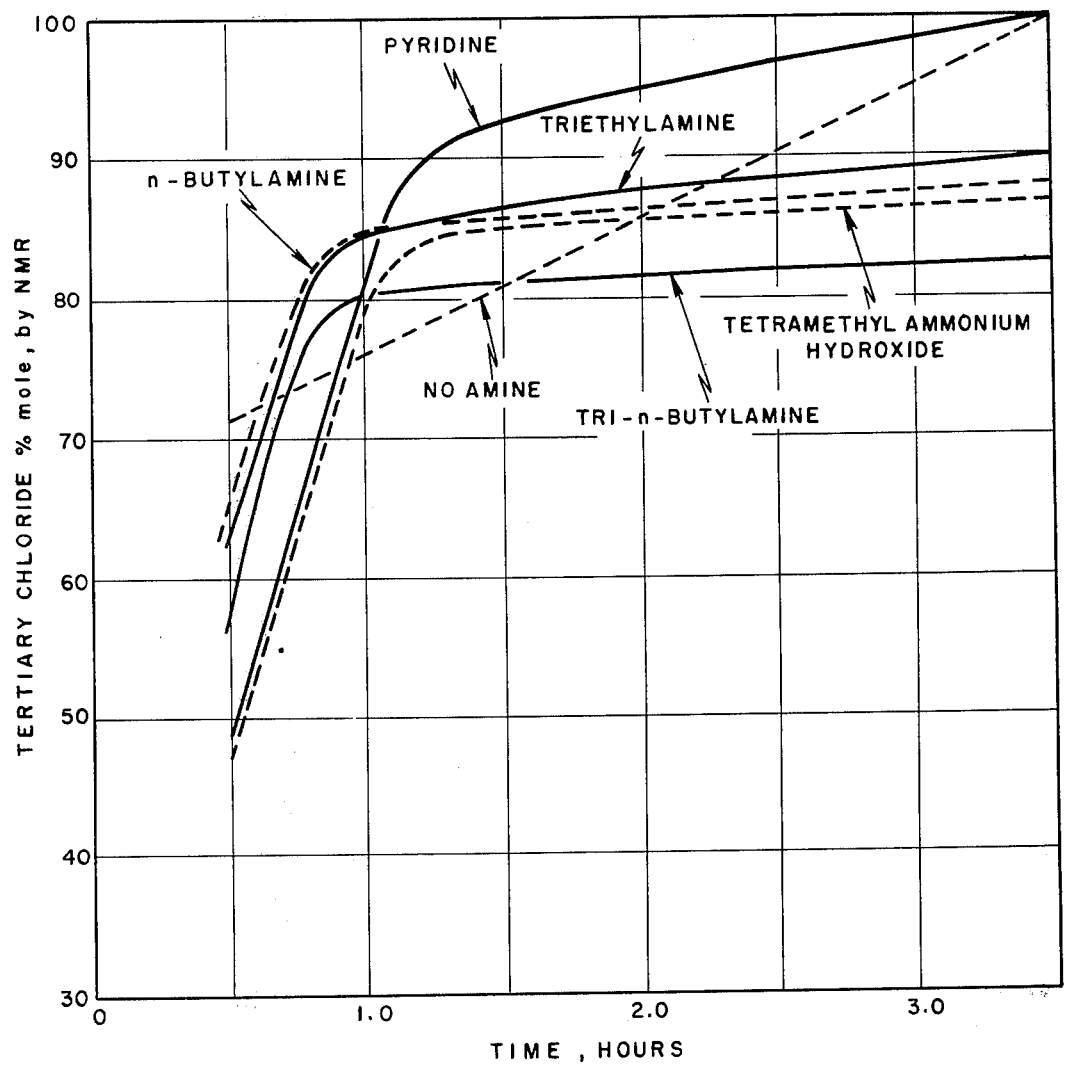
Figure 2:
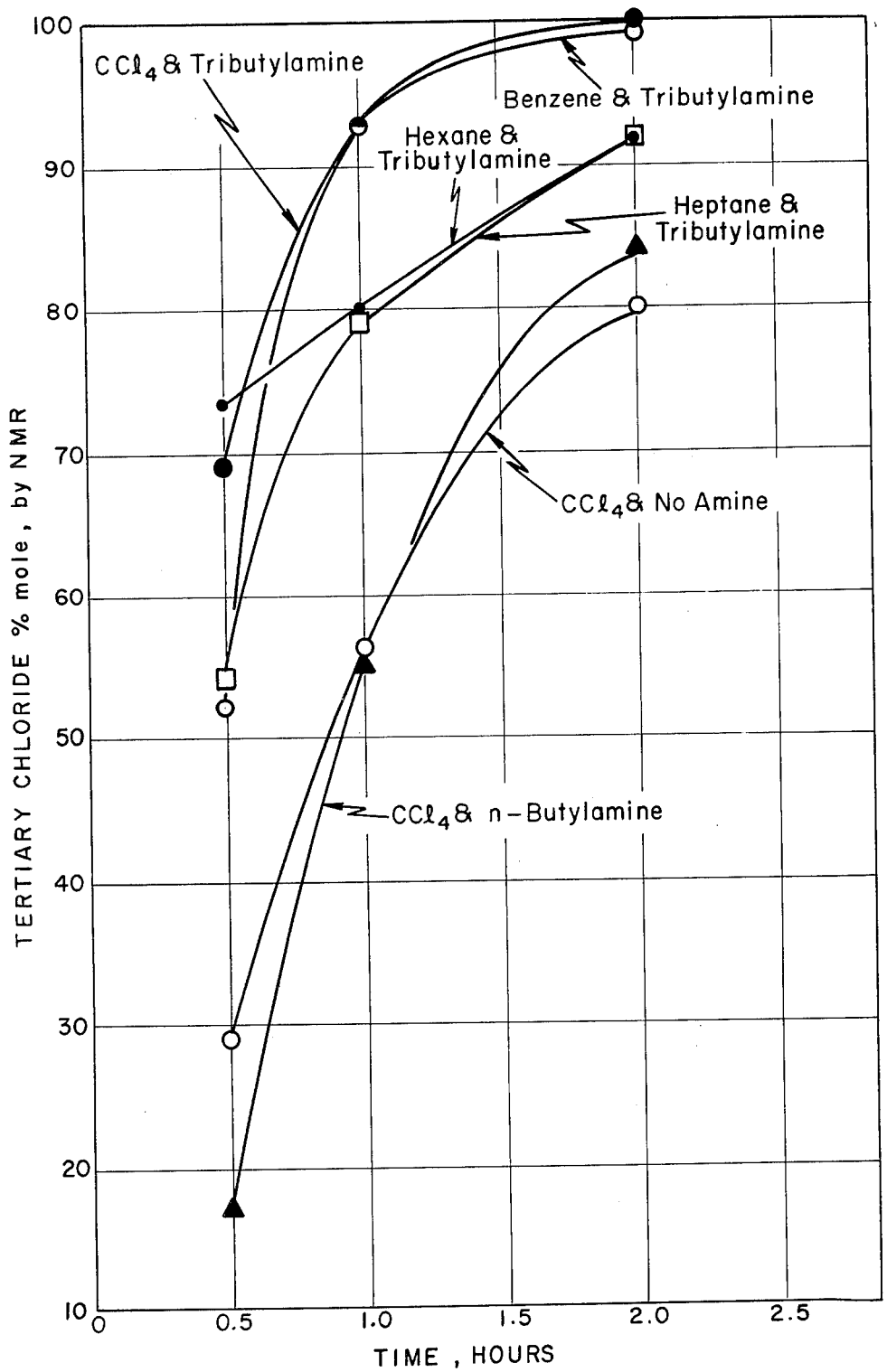

The drawings contain two figures, as follows:

FIG. 1 is a graphic illustration of the speed of the hydrochlorination reaction as influenced by various amine promoters; and FIG. 2 is a graphic illustration of the speed of the hydrochlorination reaction as influenced by different combinations of amines and solvents.

BACKGROUND OF THE INVENTION

1. Field of the Invention

This invention relates to the production of tertiary alkyl chlorides, by the hydrohalogenation of source reactants having the proper structure. The tertiary alkyl halides are formed by reaction with gaseous hydrogen halide and the corresponding olefin or tertiary alcohol. The olefin forming a tertiary alkyl halide is referred to as a "Type III" olefin, and will be of the structure:

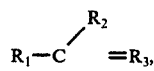

where $R_1$, $R_2$ and $R_3$ are alkyl groups.

2. Description of the Prior Art

The present invention is directed to an improvement in the process of reacting tertiary alcohols and like olefins with a hydrogen halide such as gaseous hydrogen chloride in order to form a tertiary alkyl halide product. In the past, this reaction has been recognized as being simple and easy to carry out, due to the respective reactivities of the reagents. However, it is desirable to increase the speed of the reaction in order to reduce the requisite reaction time and thereby reduce the capital investment for commercial facilities.

As far as the present inventor is aware, the use of an amine in the manner suggested in the present application is not known to the art. However, in U.S. Pat. No. 3,255,265 issued to William L. Walsh on June 7, 1966, a catalyst made up of the reaction product between an aryl sulfonic acid and an amine was suggested for use in a similar manner when preparing tertiary alkyl halides from "tertiary" (i.e., Type III) olefins. The Walsh patent does not disclose the use of a catalyst which is suitable for hydrohalogenating both tertiary alcohols and "tertiary" (Type III) olefins, nor does he show the use of an amine alone.

Walsh states:

"It is important that the amine interact with the sulfonic acid prior to exposure to reactant acids such as hydrogen chloride ... (since) hydrogen chloride salts are insoluble in hydrocarbon whereas sulfonic acid-amine salts are not only quite soluble in hydrocarbon but are even more soluble in aliphatic chloride, which is the reaction product." (Emphasis added)

In the present application, it will be noted that the amine is not reacted with an aryl sulfonic acid as suggested by Walsh. Rather, the unreacted amine is added to the reaction zone with the other reactants and possibly an inert hydrocarbon solvent.

DISCUSSION OF THE PRESENT INVENTION

The present invention relates to the formation of tertiary alkyl halides. For simplicity, however, the discussion hereinafter will be directed to the production of tertiary alkyl chlorides, which are representatives of the reactions to be expected from all of the halogens. As will be seen, the use of an amine speeds up the hydrochlorination reaction without unduly increasing the amount of dimerization (or other polymerization) which may be suffered.

Tertiary alkyl chlorides of high purity are desired as reagents in the tertiary alkylation of aromatic hydrocarbons as described in my copending application Ser. No. 101,921, now U.S. Pat. No. 3,739,039. As described in that application, selective tertiary alkylation of aromatic nuclei results in the production of compounds having utility as lubricants, either as oils or as greases. The tertiary alkyl substituted aromatic nucleus is extremely stable, since it does not have a labile benzylic hydrogen atom. In order to carry out the selective tertiary alkylation of the copending application, however, it is necessary to have tertiary alkyl chlorides of high purity and without undue amounts of secondary alkyl chloride present. The present invention is useful in producing the tertiary alkyl chlorides useful in the selective tertiary alkylation reaction claimed in the above-mentioned copending application.

The present invention employs either a tertiary alcohol or a Type III ("tertiary") olefin. The tertiary alcohol can be obtained by Grignard synthesis utilizing a suitable olefin as a primary feedstock. The olefin which can be used as a primary feedstock to Grignard synthesis, or as a reactant in the present invention, can be obtained by dimerization or higher polymerization of alpha olefins, all as is well known in the art. Each of the reactants, the reaction conditions, and the suitable chlorides are discussed separately in the sections following.

Grignard Synthesis of Alcohols. The tertiary alcohols, which may be reacted with hydrogen chloride in accordance with the present invention, may be obtained by Grignard synthesis, as is well known to the art. The Grignard reaction is expressed as follows:

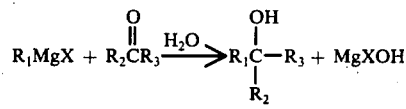

To obtain tertiary alcohols, the base feedstock is a ketone. The nature of the alkyl or aryl substituents on the tertiary alcohol are determined by the choice of the alkyl or aryl groups in the Grignard reagent and in the ketone.

In the present specification, the structure of the tertiary alcohols will be indicated by the number of carbon atoms in $R_1$, $R_2$ and $R_3$. Thus 1-1-2 would indicate a five-carbon atom tertiary alcohol, with one carbon atom in each of $R_1$ and $R_2$ and 2 carbon atoms in $R_3$. The fifth carbon atom is the tertiary carbon to which $R_1$, $R_2$ and $R_3$ are attached.

Exemplary tertiary alcohols which have been employed in the present invention are shown below in Table I.

TABLE I

| Structure | Tertiary Alcohols Grignard C No. | Ketone Source |
|---|---|---|
| 1-1-7 | 7 | $CH_3\overset{O}{\overset{\|}{C}}-CH_3$ |
| 1-1-9 | 1 | $CH_3\overset{O}{\overset{\|}{C}}-C_9H_{19}$ |
| 2-1-6 | 6 | $CH_3\overset{O}{\overset{\|}{C}}-C_2H_5$ |
| 2-1-7 | 7 | $C_3\overset{O}{\overset{\|}{C}}-C_2H_5$ |
| 2-1-8 | 8 | $CH_3\overset{O}{\overset{\|}{C}}-C_2H_5$ |
| 3-1-5 |  | (Purchased) |
| 3-1-6 | 6 | $CH_3\overset{O}{\overset{\|}{C}}-C_3H_7$ |
| 4-1-4 | 4 | $CH_3\overset{O}{\overset{\|}{C}}-OC_2H_5$ |
| 4-1-5 | 4 | $CH_3\overset{O}{\overset{\|}{C}}-C_5H_{11}$ |
| 4-1-6 | 4 | $CH_3\overset{O}{\overset{\|}{C}}-C_6H_{13}$ |

As can be seen from the above table, a large variety of tertiary alcohols can be prepared and are suitable for use in the present process. The tertiary alcohols may contain from 4 to 40 carbon atoms, preferably from 7 to 28 carbon atoms.

Type III Olefins. The present process is also suitable for use in the reaction of Type III olefins with hydrogen chloride. The Type III olefins can be obtained, as is well known to the art, by polymerization of α-olefins:

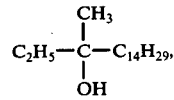

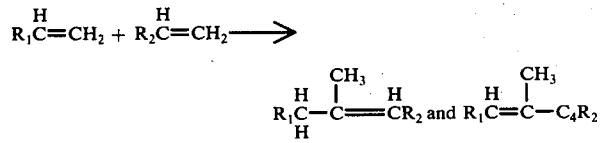

For example, the dimer, trimer and tetramer of propylene can be used, as well as disobutylene and like Type III olefins. The Type III olefins may contain from 4 to 40 carbon atoms, preferably from 7 to 28 carbon atoms.

Amine Additives. The amine additive which is to be used in the present invention includes both alkyl and aryl compounds. For example, triethylamine, n-butylamine, tributylamine, pyridine and tetramethyl ammonium hydroxide have been found to be suitable. Triethylamine and tributylamine are preferred, both because of their suitability and because of their availability. In general, any amine which is soluble in the reaction media will be suitable for use in the present invention, but some care must be used in selecting a solvent which is compatible with the chosen amine. For example, n-butylamine is effective when hexane is used as a reaction solvent, but not when carbon tetrachloride is so employed. The amines may contain from 2 to 27 carbon atoms, preferably from 6 to 15 carbon atoms.

In FIG. 1 the enhancement in reaction rate by use of the amine promoters is graphically illustrated. The data for FIG. 1 were derived from the hydrochlorination of the 2-1-14 alcohol:

$$C_2H_5-\underset{\underset{OH}{|}}{\overset{\overset{CH_3}{|}}{C}}-C_{14}H_{29},$$

using heptane as a solvent. Note that the reaction rate (as shown by the slopes of the curves) is significantly enhanced by use of the amine promoter. Particularly in continuous operations, where reaction times on the order of 1 to 1½ hours may be preferred, the reaction rates will have been sufficiently fast as to have virtually completed the reaction (since the curves become substantially flat).

By contrast, reaction without the amine promoter is essentially straight-line with time.

As will be seen hereinafter, the proper choice of solvent can provide even better enhancement of reaction rate.

Solvents. Any hydrocarbon boiling within the range from about 75° F. to about 360° F. and which is liquid and inert at the reaction temperatures will be suitable as a solvent. Normal pentane, hexane, heptane and benzene have proven to be acceptable solvents. As discussed below, carbon tetrachloride is also suitable for use with tributylamine, but not with small amounts of n-butylamine. Other chlorinated hydrocarbon solvents should also be suitable. Proper selection of solvent/amine pairs can be easily made by those skilled in the art by following the procedures in the examples hereinafter given and determining the reaction speed and specificity.

It has been found that the use of benzene or carbon tetrachloride as a solvent while employing tributylamine as a promoter leads to an enhanced reaction rate which indicates the presence of synergism. Note that in the examples later given, tributylamine and benzene or carbon tetrachloride lead to 99% conversion at only 2 hours reaction time, compared to 3½ hours for tributylamine and hexane or heptane. (With no amine promoter, Example 1 shows that 99% conversion was not reached even at 3½ hours).

Thus, the preferred promoter-solvent system for the present invention will be tributylamine with benzene or carbon tetrachloride.

The interaction between amine and solvent is shown graphically in FIG. 2. The curves in FIG. 2 were derived from the hydrochlorination of the 3-1-14 tertiary alcohol in various solvent amine systems. The alcohol structure was:

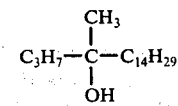

From FIG. 2 it is seen that, with carbon tetrachloride as a solvent, there is very little effect on reaction rate if n-butylamine is employed as a promoter, even when a very large excess of the amine is employed. On the other hand, tributylamine and carbon tetrachloride provide the most active system, approached closely by benzene and tributylamine. Heptane and hexane, with tributylamine, are effective solvents but do not provide the synergistic enhancement of reaction rate exhibited by carbon tetrachloride or benzene with tributylamine.

Reaction Conditions. The hydrochlorination reaction is carried out by reaction of gaseous HCl with a liquid reactant (alcohol or olefin). The temperature generally will range from 20° to 100° F. (preferably from 32° to 50° F.), a pressure from 0.5 to 100 psig (preferably from 2 to 20 psig), and a reaction time of about 0.25 to 12 hours (preferably from 0.5 to 5 hours). Lower temperatures are preferred in order to minimize polymerization.

The alcohol or olefin feedstock is preferably admixed with a solvent and with aqueous hydrochloric acid prior to or at the time of introduction into the reaction zone, although the aqueous HCl may be omitted if desired. The amine additive may be admixed with the liquid constituents before or after introduction thereof into the reaction zone, and the reaction may be carried out batchwise or continuously. In any event, the reaction mixture (dry basis) will be made up of the following components, in the proportions shown (the total being 100% by weight):

a. t-alcohol or Type III olefin feedstock, from 35 to 95 weight percent
 b. solvent, from 0 to 70 weight percent
 c. amine, from 0.3 to 15 weight percent and
 d. HCl, from 5 to 55 weight percent (dry basis).

Water, resulting from the alcohol-HCl reaction, will also be present, along with any water added with aqueous HCl. Aqueous HCl is equivalent to dry HCl and water. Where aqueous HCl is not initially added, the water phase will ultimately become saturated with HCl, and thus HCl in the water is included in HCl (dry basis).

Preferably, the reaction mixture will have the following narrower range of proportions (dry basis):

a. feedstock, from 40 to 60 weight percent
 b. solvent, from 20 to 50 weight percent
 c. amine, from 0.5 to 5 weight percent, and
 d. HCl (dry basis), from 5 to 45 weight percent.

Water will be present as above mentioned.

To the above admixture, gaseous HCl is passed in intimate contact at a rate of from 3 to 30 volumes of HCl per volume of mixture per hour, preferably from 7 to 20 v/v/hr. (expressed at standard temperature and pressure). The reaction time is measured either as the time during which gaseous HCl is passed through a batch reactor or as the liquid residence time in a continuous reactor and, as above mentioned, will generally be from 1 to 5 hours.

EXAMPLES

In order to illustrate the present invention, the following examples are given. The procedure followed in these examples was as follows.

An admixture of the feedstock, the solvent (if any), the amine and 37% aqueous HCl was formed in a 3-neck flask and cooled to the chosen beginning temperature. The pressure in the flask was essentially atmospheric. Anhydrous HCl gas was then bubbled through the admixture for varying lengths of time. In some cases, the HCl addition was suspended overnight and started again the following morning. In those cases, the time of addition is shown as two numbers separated by a plus (+) sign.

Periodically, samples were withdrawn for analysis. At the end of the reaction, the HCl addition was terminated and the reaction mixture poured over ice. Product workup included vacuum distillation (in most cases) and clay percolation (in some cases).

The results of these runs are shown in the following table.

TABLE II

Hydrochlorination of Tertiary Alcohols

| Example No. | 1 | 2 | 3 | 4 | 5 | 6 | 7 | 8 |
|---|---|---|---|---|---|---|---|---|
| Tertiary Alcohol | ← | HO, CH₃* / C / C₃H₇, C₁₄H₂₉ | | | | | | → |
| Wt. Charged, Grams | | | | | | | | |
| Alcohol | 95.0 | 95.0 | 95.0 | 95.0 | 95.0 | 95.0 | 95.0 | 95.0 |
| Tributylamine | (No Amine) | 6.2 | 6.2 | 6.2 | 6.2 | — | — | — |
| n-butylamine | — | — | — | — | — | 2.4 | 0.7 | 0.7 |
| 37% Aq. HCl | — | 3.3 | 3.3 | 3.3 | 3.3 | 3.3 | 1.0 | 10.0 |
| Distilled H₂O | 3.0 | — | — | — | — | — | — | — |
| Hexane (80 ml) | — | 53.6 | — | — | — | — | — | — |
| Heptane (80 ml) | — | — | 54.3 | — | — | — | — | — |
| Benzene (80 ml) | — | — | — | 69.9 | — | — | — | — |
| CCl₄ | 127.5 | — | — | — | 127.5 | 127.5 | 382.6 | 382.6 |
| Temperature range, ° C | <15 | 30–15 | 30–15 | 30–15 | 30–15 | <15 | <15 | <15 |
| NMR Analysis (mol %) of Chloride/Alcohol/Olefin | | | | | | | | |
| 0.5 hr. | 29-66-5 | 73-17-10 | 54-36-10 | 52-38-10 | 69-21-10 | 17-83-0 | Tr-100-0 | 21-79-tr |
| 1.0 hr. | 56-44-Tr | 80-20-Tr | 79-21-Tr | 93-7-Tr | 93-7-0 | 55-45-Tr | 13-87-0 | 58-42-0 |
| 2.0 hrs. | 80-20-0 | 92-8-Tr | 92-8-Tr | 99-0-Tr | 100-0-0 | 84-16-0 | 47-53-0 | 80-20-Tr |
| Final 3.5 hrs. | 94-6-0 | 99-Tr-Tr | 99-Tr-Tr | 99-Tr-Tr | 100-0-0 | 93-7-Tr | 88-12-0 | 91-9-Tr |

*Shorthand designation of this t-alcohol is (3-1-14).

| Example No. | 9 | 10 | 11 | 12 | 13 | 14 |
|---|---|---|---|---|---|---|
| C- | 41 | 42 | 43 | 44 | 45 | 46 |
| Tertiary Alcohol | ← | C₂H₅, CH₃*** / C / HO, C₁₄H₂₉ | | | | → |
| Wt. Charged, Grams | | | | | | |
| Alcohol | 126.7 | 126.7 | 126.7 | 126.7 | 126.7 | 126.7 |
| Tributylamine | (No amine) | — | — | 3.7 | — | ** |
| n-butylamine | — | * | — | — | 9.3 | ** | *** |

TABLE II-continued

Hydrochlorination of Tertiary Alcohols

|  |  |  |  |  |  |  |
|---|---|---|---|---|---|---|
| 37% Aq. HCl | 5.0 | 5.0 | 5.0 | 5.0 | 5.0 | 5.0 |
| Distilled H$_2$O | — | — | — | — | — | — |
| Hexane (80 ml) | 67.0 | 67.0 | 67.0 | 67.0 | 67.0 | 67.0 |
| Heptane (80 ml) | — | — | — | — | — | — |
| Benzene (80 ml) | — | — | — | — | — | — |
| C Cl$_4$ | — | — | — | — | — | — |
| Temperature range, ° C | 51-25 | 51-25 | 51-25 | 51-25 | 51-25 | 51-25 |
| NMR Analysis (mol %) of Chloride/Alcohol/Olefin |  |  |  |  |  |  |
| 0.5 hr. | 71-15-14 | 62-22-16 | 62-17-21 | 56-24-20 | 48-32-20 | 46-27-27 |
| 1.0 hr. | 76-10-14 | 85-10-5 | 85-10-5 | 85-5-10 | 80-15-5 | 80-15-5 |
| 2.0 hrs. | 86-Tr-14 | — | 86-10-14 | — | — | — |
| Final 3.5 hrs. | 100-0-Tr | 90-Tr-10 | 88-Tr-12 | 76-Tr-24 | 100-0-Tr | 87-0-13 |

*5.0 g Triethylamine
**4.0 g Pyridine
***22.5 g Tetramethyl Ammonium Hydroxide (20% in methanol)
****Shorthand designation of this t-alcohol is (2-1-14)

From the data shown in Table II, it is seen that the addition of the amine increases the speed of reaction in the earlier stages, which would allow the use of a reaction time of about one hour and together with suitable recycle streams would allow the use of facilities requiring a lower capital investment. Note particularly that the amount of chloride formed (which is shown as the first figure in the NMR analysis) is quite low at the end of the first half hour when no amine is present. See Example 1 where only 29% chloride was formed and Example 9 where 71% chloride was formed (at higher reaction temperatures). Compare Example 1 (29%) with the runs at comparable temperatures such as Examples 2 and 5 which show 73 and 69% chloride formed, respectively, and Examples 3 and 4 which show 54 and 52% chlorides formed, respectively. On the other hand, at the higher temperatures shown in Examples 9 through 14, note that at the end of one hour the example showing no amine (Example 9) has only 76% reaction as opposed to 80 to 85% in all of the other instances.

The data show that the reaction is materially speeded up by the presence of the amine, even though as the reaction time is allowed to become longer, the slow reaction does catch up with the enhanced reaction, as would be expected in these batch reactions. Note that the data show the effectiveness of several solvents, particularly hexane, heptane and benzene. The carbon tetrachloride solvent is not as good when used in conjunction with n-butylamine as are the other solvents (see Examples 6-8), but (along with benzene - see Example 4) is a preferred solvent when using tributylamine (see Example 5). Examples 10, 13 and 14 show the effectiveness of amines other than tributylamine and n-butylamine. Example 10 shows the effectiveness of triethylamine, Example 13 shows the effectiveness of pyridine, and Example 14 shows the effectiveness of tetramethylammonium hydroxide.

From the data above discussed it is therefore seen that the present invention is effective in increasing the speed of reaction.

The following examples show that olefins and alcohols derived from cyclic hydrocarbons can be treated according to the present invention.

EXAMPLE 15

In order to illustrate the present invention in the hydrochlorination of an alcohol derived from a cyclic hydrocarbon, purchased 1-n-butylcyclohexanol was treated as follows.

Apparatus used included a 2-liter flask equipped with reflux, bubbler, magnetic stirrer, thermometer and dropping tube. The flask was kept in an ice bath. Five hundred grams (3.2 moles) of 1-n-butylcyclohexanol, 1 mole (101 g) of triethylamine, and 390 grams of n-pentane were charged to the flask. Five moles (500 g) of 37% aqueous HCl were added through the dropping tube. The mixture was chilled sufficiently to keep the temperature below about 20° C., and gaseous HCl was bubbled through the mixture. Sodium chloride was added to saturate the water layer as the reaction proceeded. After five hours, the reaction was stopped, and the hydrocarbon phase washed three times with 200 ml of saturated NaCl solution. The yield of percolated, stripped product was 538 grams or 96.4% yield.

A similar run, using ether instead of n-pentane and using no amine, resulted in a percolated yield of 495 grams or only 88.8% yield, even though gaseous HCl was added over a period of 8+ hours.

EXAMPLE 16

In order to illustrate the present invention as used in hydrochlorinating olefins, the following example is given. Equipment similar to Example 15 was employed. To the flask were added one-fourth mole (25 g) of triethylamine, 60 g of 37% aqueous HCl, and one-half mole (49 g) of 3-ethyl-2-pentene. The contents of the flask were cooled to 5° C. and HCl gas was bubbled into the flask. After 1-½ hours, the reaction was terminated and the contents of the flask poured over ice-salt and washed. The yield was 41 grams of 3-chloro-3-methylpentene product and only 1 gram of polymer (bottoms).

In a similar run, using glacial acetic acid as a reaction medium and with no amine added, after five hours of HCl addition only 31 grams of chloride product were obtained, while 6 grams of polymer bottoms were formed, even though essentially the same amount (48 g) of 3-ethyl-2-pentene was used as a feedstock.

EXAMPLES 17-30

In order to show that the present invention does not result in undue polymer formation, the following examples are given. These runs were made in essentially the same manner as in Examples 1-14. The results are set out below in Table III.

TABLE III

| | | | Sludge Formation | | |
|---|---|---|---|---|---|
| Example No. | Alkyl Structure | Solvent and/or Amine | Time, Hrs. | Temperature Initial/Final ° C. | Bottoms, Wt. % |
| 17 | 2-2-2 OH | Ether | 2 + 4.5 | 3/18 | 1.1 |
| 18 | 2-2-2 OH | None | 1 (Aq. HCl) | 74/85 | 2.5 |
| 19 | 2-2-2 OH | nC$_5$-TEA | 1.7 | 25/50 | <2 |
| 20 | 2-2-2 OH | nC$_5$-TEA | 5 | 15/22 | Insignificant |
| 21 | 2-2-2 = | Acetic Acid | 3 | 5/10 | 16.2 |
| 22 | 2-2-2 = | TEA | 2.5 | 5 | 2.4 |
| 23 | 1-1-2 = | MeOH-TEA | 6.9 | −40/−29 | Insignificant |
| 24 | Diisobutylene | MeOH-TEA | 7.8 | −40 | Insignificant |
| 25 | 2-2-4 OH | nC$_5$-TEA | 5.8 | 15/20 | Insignificant |
| 26 | 3-1-3 OH | nC$_5$-TEA | 4.4 | 15/30 | Insignificant |
| 27 | 3-1-5 | Ether-TEA | 5 | 20 | 1 |
| 28 | 4-1-5 | nC5 | 5 | 5 | 2.3 |
| 29 | 4-1-6 | None | 2 + 6 | 0/10 | 11.1 |
| 30 | 1-1-14 | nC$_5$-TEA | 5 + 2 | 23/10 | 8.6 |

Key:
OH - Alcohol
MeOH - Methanol
Ether - Diethyl ether
= - Olefin
TEA - Triethylamine From the above examples it can be seen that the enhancement in reaction rate is not obtained at the cost of increased sludge formation.

Having disclosed my invention, what is to be covered by Letters Patent should be determined not by the examples herein given, but from the appended claims.

I claim:

1. In the liquid phase hydrochlorination of a Type III olefin to produce the corresponding tertiary alkyl chloride by injecting gaseous hydrogen chloride into a liquid reaction medium containing said olefin and from about 20 to about 50 weight percent of a hydrocarbon solvent which boils in the range between about 75 and about 360° F. and is an inert liquid at the hydrochlorination temperature, the improvement which comprises adding from about 0.3 to about 15 weight percent of an amine promoter selected from the group consisting of tributylamine, triethylamine, n-butylamine, tetramethylammonium hydroxide, and pyridine to said medium, injecting said gaseous hydrogen chloride into said medium at a temperature between about 20° and about 100° F. and a pressure between about 0.5 and about 100 psig, and recovering a tertiary alkyl chloride from said reaction medium.

2. A process as defined by claim 1 wherein said reaction medium contains aqueous hydrochloric acid.

3. A process as defined by claim 1 wherein said amine is tributylamine.

4. A process as defined by claim 1 wherein said amine is triethylamine.

5. A process as defined by claim 1 wherein said amine is n-butylamine.

6. A process as defined by claim 1 wherein said amine is tetraethylammonium hydroxide.

7. A process as defined by claim 1 wherein said amine is pyridine.

8. A process as defined by claim 1 wherein said olefin contains from 7 to 28 carbon atoms per molecule.

9. A process for the preparation of a tertiary alkyl chloride by the hydrochlorination of a Type III olefin which comprises preparing a liquid reaction medium containing said olefin, from about 20 to about 50 weight percent of benzene, and from about 0.3 to about 15 weight percent of tributylamine; introducing gaseous hydrogen chloride into said reaction medium while maintaining said medium at a temperature between about 20 and about 100° F. and at a pressure between about 0.5 and about 100 psig; and recovering a tertiary alkyl chloride from said reaction medium.

10. A process as defined by claim 9 wherein an aqueous hydrochloric acid solution is added to said reaction medium prior to the introduction of said gaseous hydrogen chloride.

11. A process for the preparation of a tertiary alkyl chloride by the hydrochlorination of a Type III olefin which comprises preparing a liquid reaction medium containing said olefin, from about 20 to about 50 weight percent of carbon tetrachloride, and from about 0.3 to about 15 weight percent of tributylamine; introducing gaseous hydrogen chloride into said reaction medium while maintaining said medium at a temperature between about 20 and about 100° F. and a pressure between about 0.5 and about 100 psig; and recovering a tertiary alkyl chloride from said reaction medium.

12. A process as defined by claim 11 wherein an aqueous hydrochloric acid solution is added to said reaction medium prior to the introduction of said gaseous hydrogen chloride.

* * * * *